(12) United States Patent
Podhajsky

(10) Patent No.: US 8,945,108 B2
(45) Date of Patent: *Feb. 3, 2015

(54) METHOD OF USING VASOCONSTRICTIVE AGENTS DURING ENERGY-BASED TISSUE THERAPY

(75) Inventor: Ronald J. Podhajsky, Boulder, CO (US)

(73) Assignee: Covidien AG (CH)

( * ) Notice: Subject to any disclaimer, the term of this patent is extended or adjusted under 35 U.S.C. 154(b) by 225 days.

This patent is subject to a terminal disclaimer.

(21) Appl. No.: 13/486,062

(22) Filed: Jun. 1, 2012

(65) Prior Publication Data

US 2012/0271295 A1 Oct. 25, 2012

Related U.S. Application Data

(60) Division of application No. 12/174,162, filed on Jul. 16, 2008, now Pat. No. 8,202,242, and a division of application No. 11/487,223, filed on Jul. 14, 2006, now abandoned, and a continuation-in-part of application No. 11/367,909, filed on Mar. 3, 2006, now Pat. No. 7,767,686.

(51) Int. Cl.
*A61B 18/04* (2006.01)
*A61K 31/70* (2006.01)
*A61K 31/00* (2006.01)
*A61K 31/522* (2006.01)

(52) U.S. Cl.
CPC .............. *A61K 31/00* (2013.01); *A61K 31/522* (2013.01)
USPC ................... 606/27; 514/34; 514/47; 606/33; 606/40

(58) Field of Classification Search
USPC .................................. 606/27; 514/263, 34, 47
See application file for complete search history.

(56) References Cited

U.S. PATENT DOCUMENTS

| | | | |
|---|---|---|---|
| 5,403,311 A | 4/1995 | Abele et al. | |
| 5,504,090 A | 4/1996 | Neely | |
| 5,573,772 A | 11/1996 | Downey et al. | |
| 5,840,990 A | 11/1998 | Daluge et al. | |
| 6,586,413 B2 | 7/2003 | Liang et al. | |
| 6,840,954 B2 | 1/2005 | Dietz et al. | |
| 2003/0199449 A1 | 10/2003 | Tarcha et al. | |

OTHER PUBLICATIONS

Washburn, et al., "Radiofrequency Tissue Ablation: Effect of Hepatic Blood Flow Occlusion on Thermal Injuries Produced in Cirrhotic Livers", Annals of Surgical Oncology, 10(7):773-777 (2003).
Feng, et al., "Adenosine A2 Receptor Activation Attenuates Afferent Arteriolar Autoregulation During Adenosine Receptor Saturation in Rats", Hypertension 2007; 50; 744-749 (2007).
Keddie, et al., "In vivo characterization of ZM 241385, a selective adenosine A2S receptor antagonist", European Journal of Pharmacology 301 (1996) 107-113.
D. Haemmerich, "Hepatic radiofrequency ablation-an overview of an engineering perspective", Minisymposium on applications of RF to Tissue Ablation, EMBC San Francisco (Sep. 2004).
Adair, et al., "Adenosine infusion increases plasma levels of VEGF in humans", BMC Physiology, 5: 10 (2005).
Anonymous, "Angiogenesis: A Common Pathway", Cancer Research-Health Research Institute-Orlando Regional Healthcare (Jun. 2005).
Linden J., "Adenosine in tissue protection and tissue regeneration", Mol Pharmacol, 67(5): 1406-13 (May 2005) Abstract only.
Gadaleta C., et al. "Serum vascular endothelial growth factor concentrations in hepatocellular cancer patients undergoing percutaneously radiofrequency thermal ablation", J. Chemother. 16 Suppl. 5:8-10 (Nov. 2004) Abstract only.
Mujoomdar, M., et al., "Adenosine Stimulation of Proliferation of Breast Carcinoma Cell Lines: Evaluation of the [3H] Thymidine Assay System and Modulatory Effects of the Cellular Microenvironment In Vitro" Journal of Cellular Physiology 201:429-438 (2004).
Buric, N., et al., "Review and Analysis of Vasoconstrictors in Local Anesthetics Applied in Orofacial Surgery", ACTA Stomatologica NAISSI 19(43) (Sep. 2003).
Hines-Peralta, et al. "Improved Tumor Destruction with Arsenic Trioxide and Radiofrequency Ablation in Three Animal Models", Radiology, 240(1 ):82-89 (2006).

*Primary Examiner* — Gina Justice

(57) ABSTRACT

A mammal undergoing an energy-based therapy is treated by administering at least one vasoconstrictive agent to the mammal prior to or during the procedure. The at least one vasoconstrictive agent is added in amounts sufficient to reduce or prevent vasodilation. This treatment method increases or promotes the size of the coagulation zone created after energy-based therapy.

20 Claims, No Drawings

METHOD OF USING VASOCONSTRICTIVE AGENTS DURING ENERGY-BASED TISSUE THERAPY

CROSS REFERENCE TO RELATED APPLICATIONS

The present application is a divisional of U.S. patent application Ser. No. 12/174,162 filed Jul. 16, 2008, now U.S. Pat. No. 8,202,242, which is a divisional of U.S. patent application Ser. No. 11/487,223 filed Jul. 14, 2006, now abandoned, which is a continuation-in-part of U.S. Pat. No. 7,767,686, filed Mar. 3, 2006, the entire contents of which are hereby incorporated by reference.

BACKGROUND

1. Technical Field

The present disclosure relates to application of vasoconstrictive agents for use during the energy-based tissue therapies or procedures and, more specifically, to a treatment regimen that prevents or alleviates symptoms associated with vasodilation.

2. Background of the Related Art

Energy-based tissue therapies such as ablation techniques are used clinically and in the operating room for therapeutic and surgical purposes. Such techniques eliminate tissue using energy sources such as laser, microwave, radiofrequency, high-intensity focused ultrasound, cryotherapy (such as freezing below −20 C.), conductive heating, and the like. Although energy-based therapies such as tissue ablation therapies and procedures have been successful in treating patients, these therapies and procedures are problematic in that they can lead to elevated concentrations of the purine nucleoside adenosine in treated areas. Adenosine can be problematic and counterproductive to the energy-based therapy and/or overall treatment. For example, adenosine can promote metastasis disease, angiogenesis, tumor cell proliferation, vasodilation, cardiac depression, low blood pressure, and other detrimental symptoms such as metastatic bloom. Moreover, adenosine can inhibit cell-mediated anti-tumor immune response. Vasodilation may be problematic during an energy-based therapy in that, among other things, it may reduce the size of the coagulation zone formed during an energy-based procedure.

SUMMARY

The present disclosure relates to a method of treating symptoms associated with adenosine including the step of administering to a mammalian subject undergoing an ablation procedure at least one agent in an amount effective in preventing or alleviating at least one symptom associated with an elevated concentration of adenosine in the mammalian subject. The agent may be at least one adenosine receptor antagonist such as 8SPT, MRS1754, MRS1220, MRE3008F20, MRS1523, ATL146e, or combinations of these adenosine receptor antagonists. In embodiments, the agent binds to at least one adenosine receptor in vivo.

In one embodiment, the agent is administered for the treatment of symptoms associated with adenosine such as inhibition of cell-mediated anti-tumor immune response, metastasis disease, angiogenesis, tumor cell proliferation, vasodilation, cardiac depression, low blood pressure, and combinations of these symptoms or conditions.

In another embodiment, the agent can be administered for the treatment or prevention of low blood pressure, and/or prevention of metastasis disease. The ablation procedure may be an energy-based tissue ablation.

The agent may be at least one A1 adenosine receptor antagonist, including but not limited to: 1,3-dipropyl-8-cyclopentylxanthine, 8-(4-[({[(2-aminoethyl)amino]carbonyl}oxy]-phenyl}-1,3-dipropylxanthine, N(6)-Endonorbornan-2-yl-9-methyladenine, ((S)-(−)-8-(3-Oxocyclopentyl)-1,3-dipropyl-7H-purine-2,6-dione), (3-[(4-amino)phenethyl]-8-cyclopentylexanthine, 1,3-dipropyl-8-(dicyclopropylmethyl)xanthine, and combinations of these adenosine receptor antagonists.

In another embodiment, the agent may be at least one A2 adenosine receptor antagonist, including but not limited to: 1,3-diallyl-8-(3,4,5-trim ethoxystyryl)-7-methylxanthine, 8-(3,4,5-trimethoxystyryl)-1,3,7-trimethylxanthine, 7-(2-phenylethyl)-5-amino-2-(2-furyl)-pyrazolo-[4,3-e]-1,2,4-triazolo[1,5-c]pyrimidine, 4-(2-[7-amino-2-(2-furyl[1,2,4]-triazolo[2,3-a[1,3,5]triazin-5-yl-)phenol), 8-(3-Chlorostyryl)caffeine, E)-1,3-dipropyl-7-methyl-8-(3,4-dimethoxystyryl)xanthine, enprofylline, 3-isobutyl-8-pyrrolidinoxanthine, [N-(4-cyanophenyl)-2-[4-(2,3,6,7-tetrahydro-2,6-dioxo-1,3-dipropyl-1H-purin-8-yl)-phenoxy] acetamide], and combinations of these adenosine receptor antagonists.

In yet another embodiment, the agent is at least one A3 adenosine receptor antagonist, including but not limited to: 3,6-dichloro-2'-(isopropoxy)4'-methylflavone, 6-phenyl-1,4-dihydropyridines, 6-carboxy-methyl-5,9-dihydro-9-methyl-2-phenyl-[1,2,4]-triazolo[5,1-a][2,7]naphthyridine, (3-(4-methoxyphenyl)-5-amino-7-oxo-thiazolo[3,2]pyrimidine), 9-chloro-2-(2-furanyl)[1,2,4]triazolo[1,5-c]quinazolin-5-amine, (2-(4-bromophenyl)-7,8-dihydro-4-propyl-1H-imidazo[2,1-i]purin-5(4H)-one dihydrochloride), and combinations of these adenosine receptor antagonists. The agent may be administered in a pharmaceutical composition which includes a pharmaceutically acceptable carrier or diluent.

The present disclosure further relates to a method of treating symptoms associated with adenosine comprising the step of administering to a mammalian subject undergoing an ablation procedure at least one adenosine receptor antagonist in an amount effective in preventing or alleviating at least one symptom associated with adenosine. In some embodiments, the adenosine receptor antagonist includes 8SPT, MRS1754, MRS1220, MRE3008F20, MRS1523, ATL146e, or combinations of these adenosine receptor antagonists.

The present disclosure further relates to a method of treating symptoms associated with adenosine comprising the step of administering to a mammalian subject undergoing an ablation procedure at least one adenosine receptor antagonist in an amount effective in preventing or alleviating at least one symptom associated with adenosine, wherein the adenosine receptor antagonist includes 8SPT, MRS1754, MRS1220, MRE3008F20, MRS1523, ATL146e, or combinations of these adenosine receptor antagonists. In some embodiments, the ablation procedure is a radiofrequency ablation of a cancer tumor.

The present disclosure further relates to an ablation method including the step of administering to a mammalian subject undergoing an ablation procedure at least one adenosine receptor antagonist in an amount effective to prevent or minimize vasodilation associated with an elevated concentration of adenosine in the mammalian subject. The ablation procedure produces a coagulation zone having a radius that ranges from a length of about 1 cm to about 20 cm.

In some embodiments, the present disclosure relates to an ablation method including the step of administering to a mammalian subject undergoing an ablation procedure at least one adenosine receptor antagonist in an amount effective to prevent or minimize vasodilation associated with an elevated concentration of adenosine in the mammalian subject, wherein the at least one adenosine receptor antagonist comprises 8SPT, MRS1754, MRS1220, MRE3008F20, MRS1523, ATL146e, or combinations thereof. The adenosine receptor antagonist may be administered in a pharmaceutical composition that includes a pharmaceutically acceptable carrier or diluent. The ablation may be an energy-based tissue ablation, including but not limited to radio frequency energy-based tissue ablation.

The present disclosure further relates to a method of treating symptoms associated with adenosine including the step of administering to a mammalian subject undergoing an ablation procedure at least one adenosine receptor antagonist in an amount effective in preventing or alleviating vasodilation associated with adenosine. The adenosine receptor antagonist may be 8SPT, MRS1754, MRS1220, MRE3008F20, MRS1523, ATL146e, or combinations thereof.

The present disclosure further relates to an ablation method of treating vasodilation comprising administering to a mammalian subject undergoing an ablation procedure at least one adenosine receptor antagonist in an amount effective in preventing or alleviating vasodilation. The adenosine receptor antagonists may include, but are not limited to, aminophylline, 8SPT, MRS1754, MRS1220, MRE3008F20, MRS1523, ATL146e, and combinations thereof. The ablation method may be a radiofrequency ablation of a cancer tumor. The cancer tumor may be located in the liver, kidney and/or lung.

The present disclosure further relates to a method of promoting the size of a coagulation zone formed during radiofrequency ablation procedure including, but not limited to the following step: administering adenosine antagonist to a patient; and ablating tissue in need thereof.

The present disclosure further relates to a method of preventing or eliminating vasodilation during a radiofrequency procedure including, but not limited to the following step: administering to a patient in need thereof an amount of adenosine receptor antagonist effective in preventing or reducing vasodilation due to adenosine.

The present disclosure further relates to a surgical technique including the steps of: administering at least one vasoconstrictive agent to a patient; and performing an energy-based therapy to form a coagulation zone. In some embodiments, the step of performing an energy-based therapy further comprises ablating tissue. In some embodiments, the energy-based therapy includes cardiac ablation, transmyocardial revascularization, benign prostate hyperplasia therapy, ablation of endometriosis, breast cancer treatment, hemostasis, vessel sealing, endometrial ablation, skin resurfacing, metastasis ablation, image-guided treatments, noninvasive blood flow monitoring, surgical tissue welding, tissue reshaping, laser therapy, microwave therapy, radiofrequency therapy, high-intensity focused ultrasound therapy, cryotherapy therapy, conductive heating, and/or combinations thereof.

DETAILED DESCRIPTION

Adenosine is a purine nucleoside compound having the general formula:

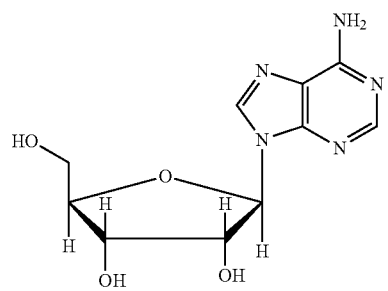

Adenosine or 9-B-D-ribofuranosyl-9H-purin-6-amine is prevalent throughout the body, and functions in various biochemical pathways by interacting with adenosine receptors that detect local changes in adenosine concentration.

The term "receptor" refers to a macromolecule capable of recognizing and selectively binding with a ligand and, after binding with the ligand, is capable of generating a physical or chemical signal that initiates the chain of events leading to the physiological response. Adenosine receptors are proteins found in animals and humans that can bind the ligand, adenosine, causing a physiological response. Adenosine receptors have been located in a variety of tissues and cells, including hippocampus, adipocytes, atrioventricle node, striatum, platelets, neutrophils, coronary vasculature and olfactory tubercule.

Four adenosine receptors are commonly referred to as A1, A2A, A2B, and A3. The stimulation of A1 receptors, among other things, can inhibit nerve cells, lower heart rate, slow AV nodal conduction, and promote vasoconstriction. The stimulation of A2A receptors is generally anti-inflammatory, and can be used to sense excessive tissue inflammation, and promote coronary vasodilation. The stimulation of A2B generally promotes vasodilation. The stimulation of A3 receptors, among other things, can both stimulate and inhibit cell growth, and promote tumor growth and angiogenesis.

Ligands that bind to the adenosine receptor causing the inhibition of the adenosine receptor physiological response are termed adenosine receptor antagonists. Likewise, ligands that bind to the adenosine receptor, thereby generating a physiological response that mimics the response caused by the adenosine receptor binding adenosine, are termed adenosine receptor agonists.

During energy-based ablation procedures or therapies inflamed or damaged tissues can release adenine nucleotides that are converted to the purine nucleoside adenosine. The degradation of extracellular nucleotides results in an elevated concentration of adenosine in the treated area, which can be problematic and counterproductive to the therapy or treatment. Accordingly, as used herein, an elevated concentration of adenosine in the mammalian subject refers to any increase in adenosine concentration in a mammalian body, including but not limited to any increase of adenosine concentration in one or more organs, tissues, systems, blood or blood parts, plasma, or the like. Moreover, an elevated concentration of adenosine in the mammalian subject refers to any higher than normal accumulation of adenosine that can detrimentally promote metastasis disease, angiogenesis, tumor cell proliferation, vasodilation, cardiac depression, low blood pressure, and combinations of these detrimental symptoms, or which can inhibit cell-mediated anti-tumor immune response.

The present disclosure relates to methods for treating or alleviating symptoms associated with adenosine by administering to a mammalian subject undergoing an ablation procedure at least one agent in an amount effective in preventing or alleviating the symptoms associated with adenosine. As used herein the word "treat," "treating" or "treatment" refers to using the active agents or compositions of the present disclosure either prophylactically to prevent undesirable adenosine symptoms, or therapeutically to ameliorate an existing undesirable condition caused by adenosine. Treatment regimens in accordance with the present disclosure improve symptoms associated with adenosine through application of pre-selected antagonists to at least one adenosine receptor.

These methods are based upon the recognition that the inhibition of the adenosine receptor physiological response prior to or during an ablation procedure provides beneficial effects that prevent or reduce angiogenesis, tumor cell proliferation, vasodilation, cardiac depression, and/or low blood pressure. Furthermore, the inhibition of the adenosine receptor physiological response prior to or during an ablation procedure prevents or reduces likelihood of metastasis disease, or the limiting effect of adenosine on cell-mediated anti-tumor immune response. Blocking of adenosine receptors maximizes the desired protective benefits, while minimizing unwanted side effects from the stimulation of adenosine receptors, such as heart block, cardiac depression, or low blood pressure. Therefore, methods and compounds are described that can promote blocking of adenosine receptors. Moreover, the methods are based upon the recognition that the inhibition of the vasodilation prior to or during an energy-based therapy provides beneficial effects such as the chemical occlusions of blood perfusion or the degree that blood flows to the treatment site.

In some embodiments, deactivation of the adenosine receptor occurs by contacting any adenosine receptor with at least one adenosine antagonist. Non-limiting examples of suitable adenosine antagonists include aminophylline, MRS 1754, MRS1220, MRE3008F20, MRS1523, ATL146e, either alone or in combination. Other receptor antagonist fall within the scope of the present disclosure including, but not limited to those adenosine antagonists listed in Table 1. Moreover, non-selective adenosine antagonists, such as 8-(p-sulfophenyl)theophylline (8SPT) can also be used in accordance with the present disclosure.

The adenosine receptor antagonists can be administered in amounts suitable to obtain the desired affect. For example, at least one adenosine receptor antagonist may be supplied in amounts sufficient to reduce or eliminate detrimental symptoms of adenosine, such as metastasis disease, angiogenesis, tumor cell proliferation, vasodilation, cardiac depression, low blood pressure, and combinations of these detrimental symptoms. Moreover, adenosine receptor antagonists can be administered in amounts suitable to prevent inhibition of cell-mediated anti-tumor immune responses caused by adenosine. In some embodiments, adenosine receptor antagonists can be supplied in an amount from about 0.1 to 200 nmol/min/kg.

However, the specific dose level for any particular individual may depend on a variety of factors: including the activity of the specific compound employed, the age, body weight, general health, sex and diet of the individual being treated; the time and route of administration; the rate of excretion; other drugs that have previously been administered; and the severity of the particular disease undergoing therapy.

The adenosine receptor antagonists can be administered during any procedure or therapy that increases the amount of adenosine in a mammalian body. Illustrative non-limiting examples of such procedures or therapies include energy-based tissue ablation such as cardiac ablation, transmyocardial revascularization, benign prostate hyperplasia therapy, ablation of endometriosis, breast cancer treatment, hemostasis, vessel sealing, endometrial ablation, skin resurfacing, metastasis ablation, image-guided treatments, noninvasive blood flow monitoring, surgical tissue welding, tissue reshaping, radiofrequency thermal ablation or radiofrequency ablation (RFA) (suitable for use in bone, and soft tissues such as liver, kidney, lung, heart, breast, lymph nodes, and nerve ganglia).

In accordance with the present disclosure, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection including perfusion and administration through catheters can be suitable. In some embodiments, methods of administration that allow rapid access to the tissue or organ being treated, such as intravenous injections for the treatment of myocardial infarction, is suitable. When an organ outside a body is being treated, perfusion can be a suitable method of administration.

Pharmaceutical compositions containing the active ingredient can be in any form suitable for the intended method of administration, including tablets, troches, lozenges, aqueous or oil suspensions, dispersible powders or granules, emulsions, hard or soft capsules, syrups or elixirs. Compositions intended for oral use can be prepared according to any method known to the art for the manufacture of pharmaceutical compositions. Tablets containing the active agent in admixture with non-toxic pharmaceutically acceptable excipients that are suitable for manufacture of tablets are acceptable.

Formulations for oral use can include hard gelatin capsules where the active ingredient is mixed with an inert solid diluent, or as soft gelatin capsules wherein the active ingredient is mixed with water or an oil medium.

The pharmaceutical compositions in accordance with the present disclosure can be in the form of a sterile injectable preparation, such as a sterile injectable suspension. This suspension may be formulated according to the known art using those suitable dispersing or wetting agents and suspending agents. In some embodiments, the sterile injectable preparation can also be a sterile injectable solution or suspension in a non-toxic parenterally acceptable diluent or solvent. Among the acceptable vehicles and solvents that may be employed are water, Ringer's solution and isotonic sodium chloride solution. In addition, suitable sterile fixed oils may be employed as a solvent or suspending medium.

The amount of active ingredient that may be combined with the carrier material to produce a single dosage form may vary depending upon the host treated and the particular mode of administration. For example, a time-release formulation intended for oral administration to humans may contain 20 to 200 μmoles of active material compounded with an appropriate and convenient amount of carrier material, which may vary from about 5 to about 95% of the total composition. In some embodiments, pharmaceutical composition can be prepared that provides easily measurable amounts for administration. For example, an aqueous solution intended for intravenous infusion should contain from about 20 to about 50 μ·moles of the active ingredient per milliliter of solution in order that infusion of a suitable volume at a rate of about 30 mL/hr can occur.

Formulations of the present disclosure suitable for oral administration may be presented as discrete units, such as: capsules, cachets or tablets, each containing a predetermined amount of the active ingredient; as a powder or granules; as a solution or a suspension in an aqueous or non-aqueous liquid;

or as an oil-in-water liquid emulsion or a water-in-oil liquid emulsion. The active ingredient may also be administered as a bolus, electuary or paste.

A tablet may be made by compression or molding, optionally with at least one accessory ingredient. Compressed tablets may be prepared by compressing in a suitable machine the active ingredient in a free flowing form, such as a powder or granules, optionally mixed with a binder, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. Tablets may optionally be provided with an enteric coating, to provide release in parts of the gut other than the stomach.

Formulations for rectal administration may be presented as a suppository with a suitable base.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions, which can be made in accordance with techniques known in the art. The formulations can be presented in unit-dose or multi-dose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

In some embodiments, suitable unit dosage formulations are those containing a daily dose or unit, daily sub-dose, or an appropriate fraction thereof, of an adenosine receptor antagonist compound.

In some particular embodiments, therapies have been developed to reduce or minimize vasodilation caused by, for example, an excess and/or elevated amount of adenosine, such as any increase in adenosine concentration in a mammalian body, including but not limited to any increase of adenosine concentration in one or more organs, including the kidneys, lungs, and/or liver, tissues, systems, blood or blood parts, plasma, or the like. An elevated concentration of adenosine in the mammalian subject further refers to any higher than normal accumulation of adenosine that can detrimentally promote vasodilation and/or blood flow induced cooling.

Adenosine accumulation is problematic for it acts as a local vasodilator and a local regulator of blood flow. Reducing or minimizing vasodilation near a tumor, promotes the formation of a coagulation zone during an energy-based therapy. Accordingly, treatments are now available for minimizing and or preventing vasodilation, as well as increasing the size of the coagulation zone formed during an energy-based therapy such as an RF ablation procedure.

Accordingly, the present disclosure relates to methods for treating, preventing and/or alleviating vasodilation such as that caused by elevated adenosine. These goals may be obtained by administering to a mammalian subject undergoing an energy-based procedure at least one vasoconstrictive agent in an amount effective in preventing or alleviating vasodilation. Accordingly, "treat," "treating" or "treatment" further refers to using the active agents or compositions of the present disclosure either prophylactically to prevent vasodilation, or therapeutically to ameliorate existing vasodilation such as that caused by adenosine. As used herein, "vasodilation" refers to relaxation or opening of at least one blood vessel. Treatment regimens in accordance with the present disclosure reduce vasodilation through application of pre-selected vasoconstrictive agents such as antagonists to at least one adenosine receptor.

These methods are based upon the recognition that the inhibition of an adenosine receptor physiological response such as vasodilation prior to or during an ablation procedure provides beneficial effects that prevent or reduce vasodilation and/or increase the size of the coagulation zone. Blocking of adenosine receptors maximizes the desired protective benefits, while minimizing unwanted side effects. Therefore, methods and compounds are described that can promote blocking of adenosine receptors.

In some embodiments, vasodilation is prevented, reduced and/or eliminated at the energy-based therapy target tissue site by administering to the patient a vasoconstrictive agent in amount sufficient to reduce blood flow in or near the energy-based therapy target tissue site. For example, a vasoconstrictive agent may be supplied in amounts sufficient to chemically occlude blood perfusion in and around the therapy target tissue site. Suitable non-limiting examples of vasoconstrictive agents include sympathomimetic amines, sympathomimetic vasopressins, adrenaline, nor-adrenalin, levonordefrin, nordefrin, phenylphrine, and combinations thereof. Additional non-limiting examples of vasoconstrictive agents include adenosine receptor antagonists as described herein.

The vasoconstrictive agent can be administered before, or during any energy-based therapy such as those therapies that cause an increased blood flow in or near the target tissue site. Illustrative non-limiting examples of such procedures or therapies include energy-based tissue ablation such as cardiac ablation, transmyocardial revascularization, benign prostate hyperplasia therapy, ablation of endometriosis, breast cancer treatment, hemostasis, vessel sealing, endometrial ablation, skin resurfacing, metastasis ablation, image-guided treatments, noninvasive blood flow monitoring, surgical tissue welding, tissue reshaping, radiofrequency thermal ablation or radiofrequency ablation (RFA) (suitable for use in bone, and soft tissues such as liver, kidney, lung, heart, breast, lymph nodes, and nerve ganglia), laser therapy, microwave therapy, radiofrequency therapy, high-intensity focused ultrasound therapy, cryotherapy therapy, conductive heating, or combinations thereof.

In some embodiments for preventing or minimizing vasodilation, deactivation of the adenosine receptor(s) that promote vasodilation occurs by contacting any adenosine receptor with at least one adenosine antagonist. Any adenosine receptor blocker that inhibits vasodilation due to the expression of adenosine can be used. Non-limiting examples of suitable adenosine antagonists include aminophylline, MRS 1754, MRS1220, MRE3008F20, MRS1523, ATL146e, either alone or in combination. Other receptor antagonist fall within the scope of the present disclosure including, but not limited to those adenosine antagonists listed in Table 1. Moreover, non-selective adenosine antagonists, such as 8-(p-sulfophenyl)theophylline (8SPT) can also be used in accordance with the present disclosure.

The adenosine receptor antagonists can be administered in amounts suitable to obtain the desired affect. For example, at least one adenosine receptor antagonist may be supplied in amounts sufficient to prevent and/or minimize vasodilation. In some embodiments for preventing and/or minimizing vasodilation, adenosine receptor antagonists can be supplied in an amount from about 0.1 to 200 nmol/min/kg.

The adenosine receptor antagonists can be administered during any procedure or therapy where vasoconstriction is desirable. Illustrative non-limiting examples of such procedures or therapies include energy-based tissue ablation such as cardiac ablation, transmyocardial revascularization, benign prostate hyperplasia therapy, ablation of endometriosis, breast cancer treatment, hemostasis, vessel sealing, endometrial ablation, skin resurfacing, metastasis ablation, image-guided treatments, noninvasive blood flow monitoring, surgical tissue welding, tissue reshaping, radiofrequency thermal ablation or radiofrequency ablation (RFA) (suitable for use in bone, and soft tissues such as liver, kidney, lung, heart, breast, lymph nodes, and nerve ganglia), laser therapy, microwave therapy, radiofrequency therapy, high-intensity focused ultrasound therapy, cryotherapy therapy, conductive heating, or combinations thereof.

The present disclosure further relates to a method for increasing the size of a coagulation zone formed during energy-based tissue ablation. Energy-based ablation therapy can be applied to tissue having a tumor. Generally, such procedures heat and kill the tissue by coagulation induced cell death. For example, a coagulation zone may be formed after heating liver tissue with an RF electrode. Such liver tissue may have a coagulation zone having a radius X. Radius X is obtained by measuring along the cross-section of the thickest portion of the tissue, and is equal to the length from center of the cross-sectional cut to the outer perimeter of the cut. In state-of-the-art procedures, radius X may be about 0.5 cm to about 3.5 cm. Accordingly, the coagulation zone may have a diameter of about 1 cm to about 7 cm. Surrounding coagulation zone may be a hyperemic rim, which is typically a zone of increased blood flow as a result of vasodilation.

As another example, a coagulation zone may be formed after heating with an RF electrode and administrating at least one vasoconstrictive agent such as adenosine receptor antagonist in an amount effective to prevent or minimize local vasodilation. The liver tissue may have a coagulation zone having a radius Y. Radius Y is obtained by measuring along the cross-section of the thickest portion of the tissue, and is equal to the length from center of the cross-sectional cut to the outer perimeter of the cut. Radius Y may be about 1 cm to about 10 cm. Accordingly, the coagulation zone may have a diameter of about 2 cm to about 20 cm. Surrounding coagulation zone may be hyperemic rim. Here, hyperemic rim may be narrower than hyperemic rim described above, due to the reduced vasodilation caused by the administration of at least one adenosine receptor antagonist in an amount effective to prevent or minimize local vasodilation. Moreover, coagulation zone may be larger than the prior mentioned coagulation zone due to the administration of at least one adenosine receptor antagonist in an amount effective to prevent or minimize local vasodilation in the liver.

TABLE 1

(Some A1, A2 and A3 receptor antagonists)

| Abbreviation | Chemical Name |
|---|---|
| A1 ANTAGONISTS | |
| DPCPX | 1,3-dipropyl-8-cyclopentylxanthine |
| XAC | 8-(4-[({[(2-aminoethyl)amino]carbonyl)oxy]-phenyl}-1,3-dipropylxanthine |
| N-0861 | N(6)-Endonorbornan-2-yl-9-methyladenine |
| KFM 19 | ((S)-(-)-8-(3-Oxocyclopentyl)-1,3-dipropyl-7H-purine-2,6-dione) |
| BW-A844U | (3-[(4-amino)phenethyl]-8-cyclopentylxanthine |
| KF 15372 | 1,3-dipropyl-8-(dicyclopropylmethyl)xanthine |
| A2 ANTAGONISTS (Subtypes A2A and A2B) | |
| DATSX | 1,3-diallyl-8-(3,4,5-trimethoxystyryl)-7-methylxanthine |
| DM TSX | 8-(3,4,5-trimethoxystyryl)-1,3,7-trimethylxanthine |
| SCH 58261 | 7-(2-phenylethyl)-5-amino-2-(2-furyl)-pyrazolo-[4,3-e]-1,2,4-triazolo[1,5-c] pyrimidine |
| ZM 241385 | 4-(2-[7-amino-2-(2-furyl[1,2,4]-triazolo[2,3-a[1,3,5]triazin-5-yl-)phenol) |
| CSC | 8-(3-Chlorostyryl)caffeine |
| KF17837 | E)-1,3-dipropyl-7-methyl-8-(3,4-dimethoxystyryl)xanthine |
| Enprofylline | 3,7-Dihydro-3-propyl-1H-purine-2,6-dione |
| IPDX | 3-isobutyl-8-pyrrolidinoxanthine |
| MRS 1754 | [N-(4-cyanophenyl)-2-[4-(2,3,6,7-tetrahydro-2,6-dioxo-1,3-dipropyl-1H-purin-8-yl)-phenoxy]acetamide] |
| A3 ANTAGONISTS | |
| MRS 1067 | 3,6-dichloro-2'-(isopropoxy)4'-methylflavone |
| MRS 1097 | 6-phenyl-1,4-dihydropyridines |
| L-249313 | 6-carboxy-methyl-5,9-dihydro-9-methyl-2-phenyl-[1,2,4]-triazolo [5,1-a][2,7]naphthyridine |
| L-268605 | (3-(4-methoxyphenyl)-5-amino-7-oxo-thiazolo[3,2]pyrimidine) |
| CGS15943 | 9-chloro-2-(2-furanyl)[1,2,4]triazolo[1,5-c]quinazolin-5-amine |
| KF26777 | (2-(4-bromophenyl)-7,8-dihydro-4-propyl-1H-imidazo[2,1-i]purin-5(4H)-one dihydrochloride) |

The following examples are given for the purpose of illustrating the present disclosure and are not intended to limit the scope in any way.

Example I

A 65 year old female weighing 130 pounds with liver tumor is undergoing RF ablation of 5 cm tumor located in liver. During the RF ablation the patient is simultaneously administered adenosine receptor antagonist in an amount sufficient to, in vivo, block A1, A2, A3 adenosine receptors immediately adjacent to the tumor. The ablation step is performed by delivering electrical current of about 500 kHz between the electrode and a ground pad. Tissue is heated by, among other things, thermal conduction. The temperature of the tissue depends upon, among other things, thermal and electrical tissue properties, and blood perfusion. Her liver is a well perfused organ with perfusion rates of around 1 L/kg/min (with tumor having a lower perfusion rate). By blocking the adenosine receptors immediately adjacent to the tumor, local vasodilation adjacent to the tumor is prevented. The hyperemic rim is reduced and the coagulation zone increased in size compared to a similar procedure without adenosine receptor antagonist administered to the patient.

Example II

A 60 year old male weighing 155 pounds with liver tumor is undergoing energy-based therapy of 6 cm tumor located in liver. During the energy-based therapy the patient is simultaneously administered at least one vasoconstrictive agent in an amount sufficient to reduce blood flow in and immediately adjacent to the tumor. The energy-based therapy is performed by delivering electrical current of about 500 kHz between the electrode and a ground pad. Tissue is heated by, among other things, thermal conduction. The temperature of the tissue depends upon, among other things, thermal and electrical tissue properties, and blood perfusion. His liver is a well perfused organ with perfusion rates of around 1 L/kg/min (with tumor having a lower perfusion rate). Vasodilation in and around the tumor is prevented. The hyperemic rim is reduced and the coagulation zone increased in size compared to a similar procedure without vasoconstrictive agent administered to the patient.

While several embodiments of the disclosure are described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A surgical technique comprising:
   administering at least one A3 adenosine receptor antagonist to a patient; and
   performing an energy-based therapy to form a coagulation zone.

2. A surgical technique in accordance with claim 1, wherein the step of performing an energy-based therapy further comprises ablating tissue.

3. A surgical technique in accordance with claim 1, wherein the energy-based therapy comprises cardiac ablation, transmyocardial revascularization, benign prostate hyperplasia therapy, ablation of endometriosis, breast cancer treatment, hemostasis, vessel sealing, endometrial ablation, skin resurfacing, metastasis ablation, image-guided treatments, noninvasive blood flow monitoring, surgical tissue welding, tissue reshaping, laser therapy, microwave therapy, radiofrequency therapy, high-intensity focused ultrasound therapy, cryotherapy therapy, conductive heating, or combinations thereof.

4. A surgical technique in accordance with claim 1, wherein the coagulation zone is formed after heating with an RF electrode and administrating at least one adenosine receptor antagonist.

5. A surgical technique in accordance with claim 1, wherein the energy based therapy produces a coagulation zone having a radius.

6. A surgical technique in accordance with claim 5, wherein the radius has a length of about 1 cm to about 10 cm.

7. A surgical technique in accordance with claim 5, wherein the radius is greater than 1 cm.

8. A surgical technique in accordance with claim 1, wherein the coagulation zone has a diameter of about 2 cm to about 20 cm.

9. A surgical technique in accordance with claim 1, wherein the at least one A3 adenosine receptor antagonist is administered in an amount effective to prevent or minimize local vasodilation.

10. A surgical technique in accordance with claim 1, wherein the at least one A3 adenosine receptor antagonist is administered simultaneously to performing the energy-based therapy in an amount effective to prevent or minimize local vasodilation.

11. A surgical technique in accordance with claim 1, wherein the at least one A3 adenosine receptor antagonist is administered prior to performing the energy-based therapy in an amount effective to prevent or minimize local vasodilation.

12. A surgical technique in accordance with claim 1, wherein in vivo, the at least one A3 adenosine receptor antagonist binds to at least one adenosine receptor.

13. A surgical technique in accordance with claim 1, wherein the at least one A3 adenosine receptor antagonist is administered in a pharmaceutical composition that includes a pharmaceutically acceptable carrier or diluent.

14. A surgical technique in accordance with claim 1, wherein the at least one A3 adenosine receptor antagonist is selected from the group consisting of 3,6-dichloro-2'-(isopropoxy)4'-methylflavone, 6-phenyl-1,4-dihydropyridines, 6-carboxy-methyl-5,9-dihydro-9-methyl-2-phenyl-[1,2,4]-triazolo[5,1-a][2,7]naphthyridine, (3-(4-methoxyphenyl)-5-amino-7-oxo-thiazolo[3,2]pyrimidine), 9-chloro-2-(2-furanyl)[1,2,4]triazolo[1,5-c]quinazolin-5-amine, (2-(4-bromophenyl)-7,8-dihydro-4-propyl-1H-imidazo[2,1-i] purin-5(4H)-one dihydrochloride), and combinations thereof.

15. A surgical technique in accordance with claim 1, wherein the at least one A3 adenosine receptor antagonist comprises 3,6-dichloro-2'-(isopropoxy)4'-methylflavone.

16. A surgical technique in accordance with claim 1, wherein the administering step includes treatment of symptoms associated with adenosine including tumor cell proliferation.

17. A surgical technique in accordance with claim 1, wherein the administering step includes administering the adenosine receptor antagonist immediately adjacent to tissue being treated.

18. A surgical technique in accordance with claim 1, wherein the at least one A3 adenosine receptor antagonist is administered in an amount from about 0.1 to about 200 nmol/min/kg.

19. A surgical technique in accordance with claim 1, further comprising administering at least one A1 adenosine receptor antagonist in combination with the at least one A3 adenosine receptor antagonist.

20. A surgical technique in accordance with claim 1, further comprising administering at least one A2 adenosine receptor antagonist in combination with the at least one A3 adenosine receptor antagonist.

* * * * *